US00PP23746P2

(12) United States Plant Patent
Müller

(10) Patent No.: US PP23,746 P2
(45) Date of Patent: Jul. 16, 2013

(54) ***COTONEASTER* PLANT NAMED 'LEMON FUNKY'**

(50) Latin Name: *Cotoneaster dammeri*
Varietal Denomination: Lemon Funky

(76) Inventor: Hans Jürgen Müller, Kornwestheim (DE)

( * ) Notice: Subject to any disclaimer, the term of this patent is extended or adjusted under 35 U.S.C. 154(b) by 126 days.

(21) Appl. No.: 13/066,366

(22) Filed: Apr. 13, 2011

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — June Hwu
(74) *Attorney, Agent, or Firm* — Mark P. Bourgeois

(57) ABSTRACT

A new cultivar of *Cotoneaster* plant named 'Lemon Funky' that is characterized by young foliage that is yellow and matures to yellow-green, grey-purple stems, green-white flowers and a prostrate habit.

1 Drawing Sheet

Botanical classification: *Cotoneaster dammeri.*
Variety denomination: 'Lemon Funky'.

BACKGROUND OF THE INVENTION

The present invention relates to a new and distinct cultivar of *Cotoneaster* plant botanically known as *Cotoneaster dammeri* and hereinafter referred to by the cultivar name 'Lemon Funky'.

'Lemon Funky' was discovered as a branch mutation on an unnamed *Cotoneaster dammeri* cultivar in an outdoor bed of commercially grown unnamed *Cotoneaster dammeri* cultivars in a cultivated area of Kornwestheim, Germany. 'Lemon Funky' was discovered in the Spring of 2008.

Asexual reproduction of the new cultivar 'Lemon Funky' first occurred by terminal cuttings in the Summer of 2008 in Kornwestheim, Germany. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Cotoneaster* cultivar 'Lemon Funky'. These traits in combination distinguish 'Lemon Funky' as a new and distinct cultivar apart from other existing known varieties of *Cotoneaster.*

1. *Cotoneaster* 'Lemon Funky' exhibits young foliage that is yellow and matures to yellow-green.
2. *Cotoneaster* 'Lemon Funky' exhibits grey-purple stems.
3. *Cotoneaster* 'Lemon Funky' exhibits green-white flowers.
4. *Cotoneaster* 'Lemon Funky' exhibits a prostrate habit.

The closest comparison cultivar is the parent unnamed *Cotoneaster dammeri* cultivar.

'Lemon Funky' is distinguishable from the unnamed parent cultivar by the following characteristics:

1. *Cotoneaster* 'Lemon Funky' has young foliage that is yellow and matures to yellow-green. The young foliage of the parent cultivar is yellow-green.

2. *Cotoneaster* 'Lemon Funky' exhibits grey-purple stems. The stems of the parent cultivar are grey-green.

BRIEF DESCRIPTION OF THE DRAWING

The accompanying photograph illustrates the distinguishing traits of *Cotoneaster* 'Lemon Funky'. The plant in the photograph shows an overall view of a 1 year old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Cotoneaster* cultivar named 'Lemon Funky'. Data was collected in Kornwestheim, Germany from 1 year old glass greenhouse grown plants in 9 cm. diameter containers. The time of year was Spring and the average temperature was 15 degrees Centigrade during the day and 5 degrees Centigrade at night. The light level was 3000 to 4000 lux. No photoperiodic treatments were used. Color determinations are in accordance with The Royal Horticultural Society Colour Chart 2007 edition, except where general color terms of ordinary dictionary significance are used. The growing requirements are similar to the species. 'Lemon Funky' has not been tested under all possible conditions and phenotypic differences may be observed with variations in environmental, climatic, and cultural conditions, however, without any variance in genotype.

Botanical classification: *Cotoneaster* 'Lemon Funky'.
Annual or perennial: Perennial.
Parentage: 'Lemon Funky' was discovered as a branch mutation on an unnamed *Cotoneaster dammeri* cultivar.
Vigor: Strong.
Growth habit: Creeping.
Plant shape: Prostrate.
Suitable container size: 9 to 12 cm. pots.
Height: 40 cm. in height.
Width: 65 cm. in width.
Low temperature tolerance: −2° Centigrade.
High temperature tolerance: 30° Centigrade.

Propagation: Terminal cuttings.
Crop time: Approximately 12 months.
Root system: Fine and fibrous.
Stem:
*Basal branching.*—Yes.
*Average number of lateral branches.*—3 to 4.
*Pinching.*—Yes.
*Lateral branch diameter.*—3 mm. in diameter.
*Lateral branch length.*—40 cm. in length.
*Internode length.*—1.5 cm.
*Stem shape.*—Round.
*Stem aspect.*—Prostrate.
*Stem strength.*—Moderate.
*Stem texture.*—Smooth.
*Stem color.*—183A.
*Pubescence.*—Absent.
Foliage:
*Leaf characteristics.*—Young leaves are evergreen, older leaves are shed in late autumn.
*Leaf arrangement.*—Alternate.
*Compound or single.*—Single.
*Number of leaves per lateral branch.*—12 to 14.
*Leaf shape.*—Ovate.
*Leaf apex.*—Obtuse.
*Leaf base.*—Acuminate.
*Leaf dimensions.*—4 cm. in length and 2 cm. in width.
*Texture.*—Glabrous both sides.
*Pubescence.*—Absent.
*Leaf margin.*—Entire.
*Venation pattern.*—Pinnate.
*Young leaf color (upper surface).*—1A.
*Young leaf color (lower surface).*—1A.
*Mature leaf color (upper surface).*—147A.
*Mature leaf color (lower surface).*—148C.
*Fall leaf color (upper surface).*—10D.
*Fall leaf color (lower surface).*—10D.
*Vein color (upper surface).*—144C.
*Vein color (under surface).*—144D.
*Leaf attachment.*—Petiolate.
*Petiole dimensions.*—5 mm. in length and 1 mm. in diameter.
*Petiole texture.*—Smooth.
*Petiole color.*—144D.
*Durability of foliage to stress.*—Strong.
Flower:
*Inflorescence arrangement.*—Solitary in axils.
*Inflorescence dimensions.*—3 mm. in height and 2 mm. in width.
*Quantity of flowers per inflorescence.*—1.
*Quantity of flower buds per lateral stem.*—20.
*Quantity of flowers per lateral stem.*—20.
*Quantity of flowers and buds per plant.*—Average 60.
*Natural flowering season.*—April to May.
*Time to flower.*—1 year.
*Rate of flower opening.*—Every 2 to 3 days.
*Fragrance.*—Slight honey scent.
*Flower bud length.*—2 mm.
*Flower bud diameter.*—2 mm.
*Flower bud shape.*—Ovate.
*Bud color.*—157A.
*Rate of bud opening.*—2 to 3 days.
*Flower aspect.*—Outward.
*Flower shape.*—Radiate.
*Flower dimensions.*—3 mm. in diameter and 2 mm. in height.
*Flower longevity.*—7-10 days.
*Number of petals.*—5.
*Fused or unfused.*—Fused.
*Petal shape.*—Ovate.
*Petal texture.*—Smooth both sides.
*Petal margin.*—Entire.
*Petal apex.*—Obtuse.
*Petal base.*—Cuneate.
*Petal length.*—1.5 mm.
*Petal width.*—1.5 mm.
*Petal color when opening (upper side).*—157A.
*Petal color when opening (under side).*—157C.
*Petal color fully opened (upper side).*—157A.
*Petal color fully opened (under side).*—157C.
*Petal color fading to.*—157C.
*Self-cleaning or persistent.*—Self-cleaning.
Sepals:
*Sepal appearance.*—Clasping.
*Number of sepals.*—5.
*Sepal shape.*—Lanceolate.
*Sepal margin.*—Entire.
*Sepal apex.*—Acuminate.
*Sepal base.*—Cuneate.
*Sepal dimensions.*—8 mm. in length and 2 mm. in width.
*Young sepal color (upper side).*—144C.
*Young sepal color (under side).*—144C.
*Mature sepal color (upper side).*—144C.
*Mature sepal color (under side).*—144C.
Calyx:
*Calyx shape.*—Lyrate.
*Calyx dimensions.*—8 mm. in length and 2 mm. in diameter.
Peduncle:
*Peduncle dimensions.*—1.5 mm in length and 0.5 mm. in diameter.
*Peduncle angle.*—40 degrees from vertical.
*Peduncle strength.*—Strong.
*Peduncle color.*—144C.
Reproduction organs:
*Stamen number.*—5.
*Anther shape.*—Reniform.
*Anther size.*—1.0 mm.
*Anther color.*—157A.
*Pollen color.*—157A.
*Amount of pollen.*—Moderate.
*Pistil number.*—1.
*Pistil length.*—1.5 mm.
*Stigma shape.*—Ovate.
*Stigma color.*—157B.
*Style length.*—1 mm.
*Style color.*—157B.
*Ovary color.*—157B.
Fruit and seed production: Fruit and seed production has not been observed.
Disease and pest resistance: Disease and pest resistance has not been observed.

The invention claimed is:

1. A new and distinct variety of *Cotoneaster* plant named 'Lemon Funky' as described and illustrated.

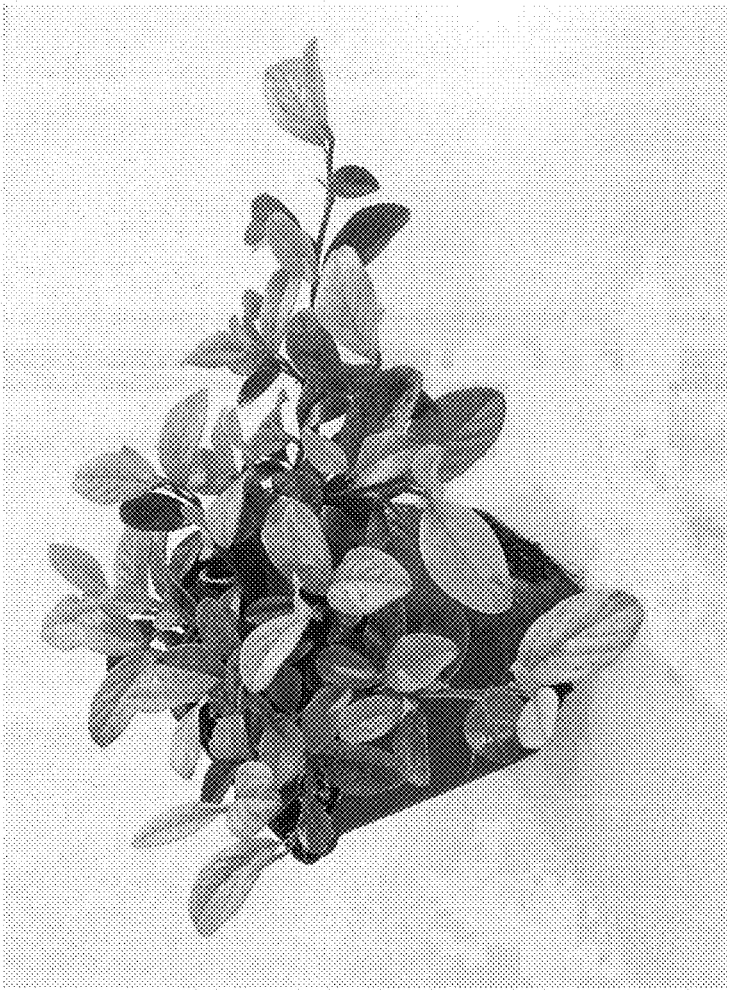

* * * * *